(12) United States Patent
O'Brien et al.

(10) Patent No.: US 6,826,982 B2
(45) Date of Patent: Dec. 7, 2004

(54) METHOD AND APPARATUS FOR DETECTION OF STRUCTURAL DAMAGE

(75) Inventors: Edwin W O'Brien, Bristol (GB); Andrew R Ibbotson, Bristol (GB)

(73) Assignee: BAE Systems plc, Farnborough (GB)

( * ) Notice: Subject to any disclaimer, the term of this patent is extended or adjusted under 35 U.S.C. 154(b) by 0 days.

(21) Appl. No.: 10/275,701

(22) PCT Filed: May 18, 2001

(86) PCT No.: PCT/GB01/02213
§ 371 (c)(1), (2), (4) Date: Nov. 8, 2002

(87) PCT Pub. No.: WO01/94934
PCT Pub. Date: Dec. 13, 2001

(65) Prior Publication Data
US 2003/0140701 A1 Jul. 31, 2003

(30) Foreign Application Priority Data
Jun. 8, 2000 (GB) .............................. 0013932

(51) Int. Cl.$^7$ .............................................. G01N 29/04
(52) U.S. Cl. .......................... 79/587; 702/39; 702/188; 702/197
(58) Field of Search .................... 73/587, 597, 598; 702/35, 36, 39, 54, 188, 189, 196, 197

(56) References Cited

U.S. PATENT DOCUMENTS

| | | | | |
|---|---|---|---|---|
| 4,535,629 A | * | 8/1985 | Prine | 73/587 |
| 4,979,124 A | * | 12/1990 | Sachse et al. | 702/38 |
| 6,399,939 B1 | * | 6/2002 | Sundaresan et al. | 250/231.1 |

FOREIGN PATENT DOCUMENTS

| | | |
|---|---|---|
| EP | 0 470 654 A | 2/1992 |
| WO | 96/28727 A | 9/1996 |
| WO | 97/11364 A | 3/1997 |

\* cited by examiner

Primary Examiner—Hezron Williams
Assistant Examiner—Rose M. Miller
(74) Attorney, Agent, or Firm—Nixon & Vanderhye P.C.

(57) ABSTRACT

The entire contents of these applications are incorporated herein by reference. A method and apparatus for detecting and monitoring fractures in a structure by monitoring acoustic energy transmitted within the structure by receiving continuously over a period of time electrical signals from a plurality of acoustic tranducers carried by the structure in a pulse processor to form data bursts from pulses in the signals and deriving, for each of a plurality of the data bursts, delta-t values representing the differences between burst arrival times at each sensor, the delta-t values forming a delta-t pattern, and generating a damage indication signal when the delta-t pattern is repeated to a predetermined degree.

21 Claims, 6 Drawing Sheets

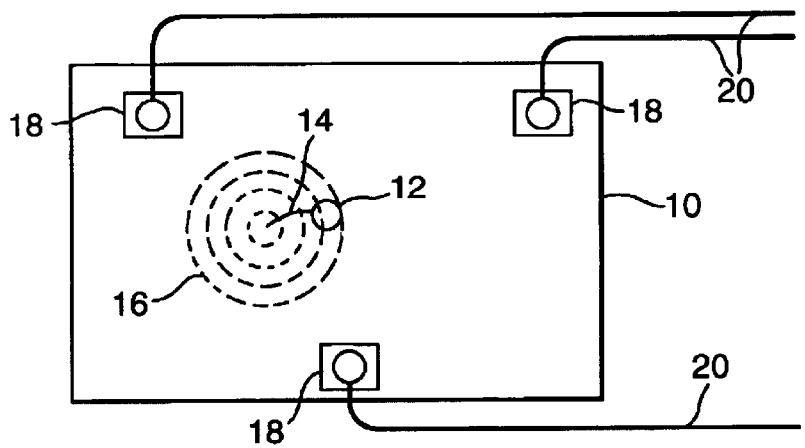
Fig.1.
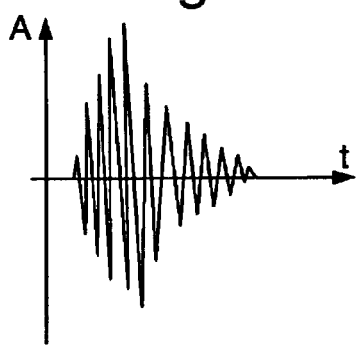
Fig.3.
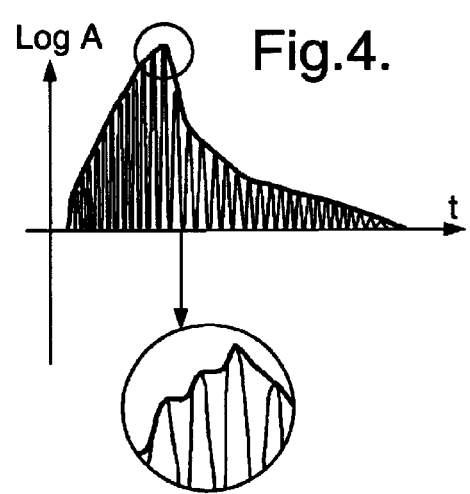
Fig.4.
Fig.5.
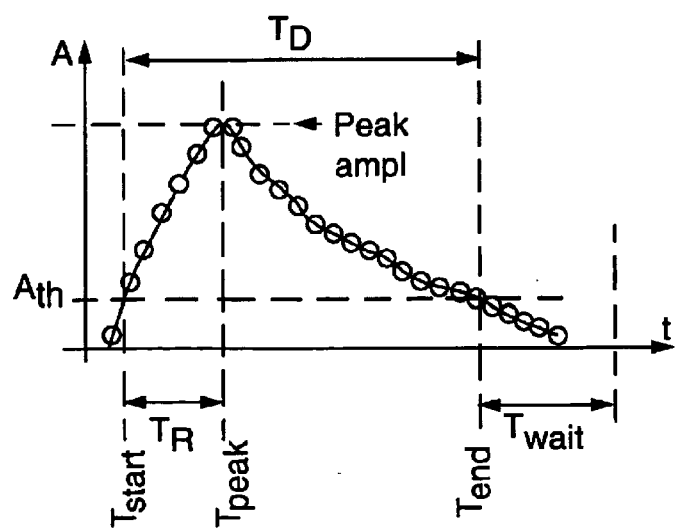

METHOD AND APPARATUS FOR DETECTION OF STRUCTURAL DAMAGE

This application is the US national phase of international application PCT/GB01/02213, filed in English on 18 May 2001 which designated the US. PCT/GB01/02213 claims priority to GB Application No. 0013932.9 filed 8 Jun. 2000. The entire contents of these applications are incorporated herein by reference.

BACKGROUND OF THE INVENTION

1. Field of the Invention

This invention relates to a method of detecting and monitoring damage in a structure by monitoring acoustic energy transmitted within the structure. The invention relates, in addition, to damage detection and monitoring apparatus and to a structure including a plurality of acoustic transducers.

2. Discussion of Prior Art

It is known that stable crack growth in metallic structures due to fatigue and stress corrosion occurs due to a process of slow embrittlement of the material as a result of stress concentration within a short distance of the crack tip. This is followed by crack advance to a zone boundary in a series of discrete transgranular or intergranular microfracture events, the advance being arrested at the zone boundary by tough undegraded material. This cycle then repeats. The microfracture events are explosive in nature, those occurring in steel and aluminium alloys typically occurring with a mean velocity in the range of from 250 to 500 meters per second.

Structures in which fracturing of this kind is a particular problem include offshore oil and gas installations, aircraft, and pressure vessels. The invention has primary application to metallic structures in those technical fields, but it is not limited by the field of application nor by the material used.

The applicants recognise that crack development, as described above, produces wideband ultrasonic energy (acoustic emissions) within the structure which can be detected using transducers. The range of detection of acoustic pulses depends on such factors as the material thickness, component shape, surrounding fluid medium and interference from background noise.

SUMMARY OF THE INVENTION

It is an object of this invention to provide a method aiding the detection and/or location of damage sites of a range of sizes.

According to a first aspect of this invention, a method of detecting and monitoring damage in a structure comprises: receiving continuously over a period of time electrical signals from a plurality of acoustic transducers carried by the structure; and in a pulse processor, (a) forming digital representations pulses from the electrical signals to form data bursts, (b) selecting data bursts that occur in a predetermined time window to form a group of data bursts, (c) deriving, for each of the selected data bursts, delta-t values representing the differences between the times of occurrence of the pulses represented by the selected data bursts in the groups, the delta-t values forming a delta-t pattern, and (d) generating a significant event indication signal when the delta-t pattern is repeated to a predetermined degree in different groups of selected data bursts.

According to a second aspect of the invention, apparatus for use in the detection and monitoring of damage in a structure comprises: a plurality of acoustic transducers for mounting on a structure to be monitored; a signal conditioning stage coupled to the transducers and arranged to derive pulses corresponding to acoustic events sensed by the transducers; and a pulse processor unit comprising an analogue-to-digital converter (ADC) stage coupled to the signal conditioning stage and a digital signal processing stage including (a) digitising means to digitise pulses from received signals to form data bursts, b)selection means configured to select data bursts to form a group of data bursts emanating from the signals received from different transducers in a respective time window, (c) means arranged to derive, for each of the selected data bursts, delta-t values representing the differences between the times of occurrence of the data bursts in the group, the delta-t values forming a delta-t pattern, and (d) a correlator arranged to generate a significant event indication signal when the delta-t pattern is repeated to a predetermined degree in different groups.

The invention also includes a structure which is monitored for damage due to cyclic loading, wherein the structure comprises a plurality of structural members, a plurality of groups of acoustic transducers, each group mounted on a respective structural member, and a signal processing unit coupled to the transducers and arranged to detect groups of data bursts each comprising a data burst representing pulses in signals received from respective transducers of one of the groups of transducers during a sampling time interval, and to derive, for each of the data bursts, timing information relating to the times of arrival of the pulses forming the group, the signal processing unit further comprising a correlator arranged to generate a significant event indication signal when the timing pattern is repeated to a predetermined degree in different groups from the said group of transducers.

The processing unit is configured to have a plurality of channels, each channel handling signals from a respective transducer.

Each group of data bursts is typically composed of data bursts in different respective channels of the unit occurring within a respective time window, continuous data acquisition occurring over long time periods, typically in the order of hours to several months, during which bursts are received continuously from consecutive or overlapping such time windows. Depending on the nature of the structure and the loading under which it is placed, relevant significant acoustic events due, for instance, to growth of a crack may occur only once in millions of data burst windows, typical causes being extreme weather conditions in the case of an oil rig, or certain high load events during an aircraft's flight (for instance takeoff and landing, or turbulence).

Damage, including fractures or cracks in metallic structures and fretting in composite structures invariably give rise to these significant acoustic events which the method and apparatus according to the invention aim to detect and to indicate as a so-called significant event indication signal.

The ability to detect and monitor crack growth sites of a wide range of sizes and different acoustic emission intensities is enhanced if groups of data bursts are correlated using real time filtering via a primary filter with a first set of characteristics selected to detect new fractures, and secondary filters which are adaptively created with a second set of characteristics to monitor fractures which have already been detected using the primary filter. The secondary filter characteristics are tailored to the characteristics of groups of data bursts emanating from these detected fractures. Such groups are then diverted from the primary filter to be processed instead in the secondary filter. This allows, for instance, high and low intensity damage sites to be simultaneously monitored without substantial loss of data due to such causes as lack of processing capacity or storage device overflow.

Other preferred features are contained in the dependent claims accompanying this description.

BRIEF DESCRIPTION OF THE DRAWINGS

The invention will now be described by way of example with reference to the drawings in which:

FIG. 1 is a diagram showing a structural member carrying a plurality of acoustic transducers;

FIG. 3 is a waveform diagram showing a typical pulse from an acoustic transducer due to a fracture event in the structural member;

FIG. 4 is a composite waveform diagram of the output signal from a logarithmic amplifier in one channel of the apparatus when fed with a pulse such as that shown in FIG. 3;

FIG. 5 is a waveform diagram illustrating the digitisation of the output waveform shown in FIG. 4;

DETAILED DISCUSSION OF EMBODIMENTS

Figure 2:
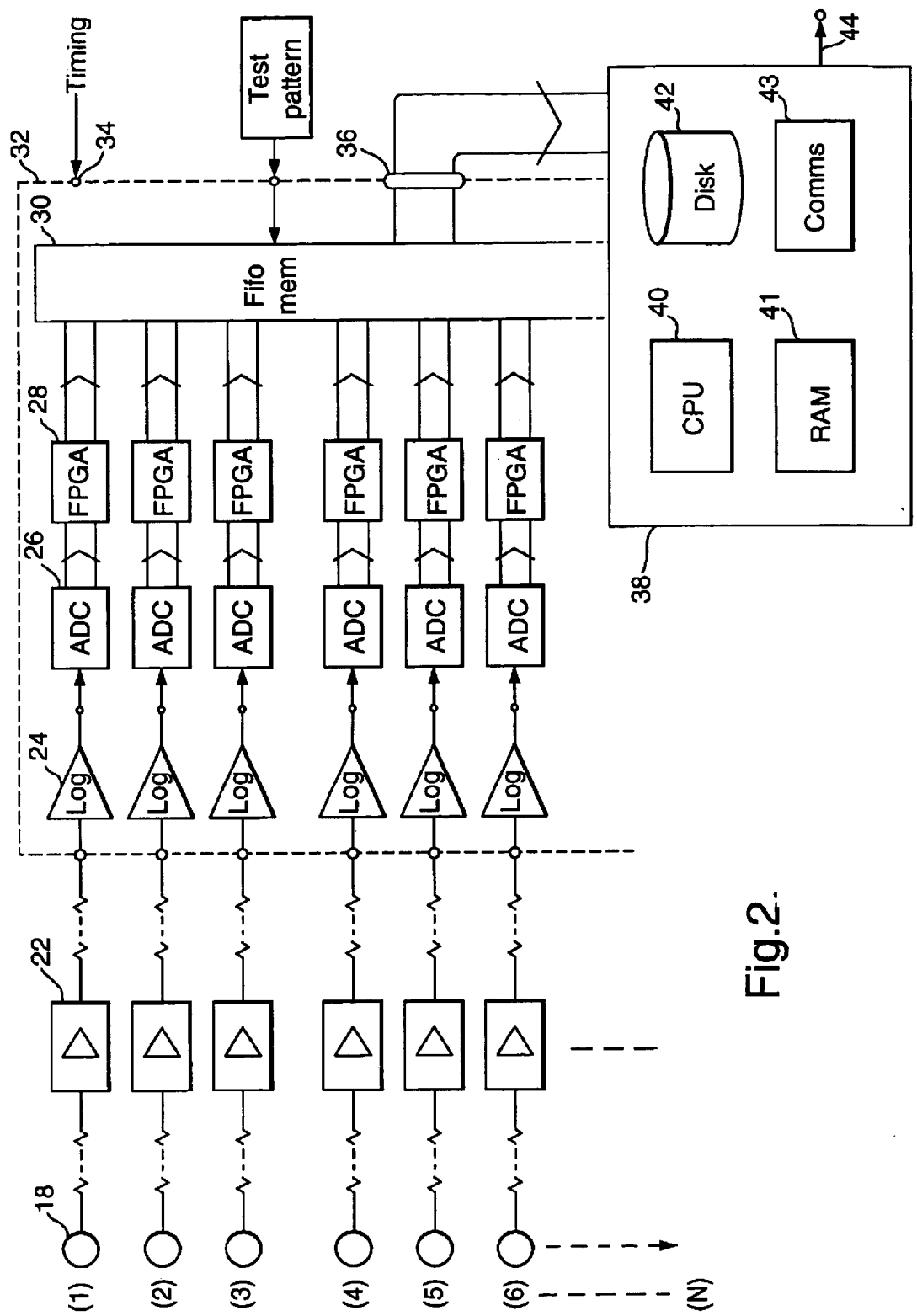
FIG. 2 is a block diagram of multiple-channel damage detection apparatus in accordance with the invention.

Referring to FIG. 1, consider a simple planar structure 10 having a bolt hole 12. When the structure is loaded, the bolt hole 12 produces a stress concentration which may give rise to a crack 14. Typically such a crack forms when the member 10 is subjected to cyclic loading. The crack grows in a series of microscopic fracture events at or near peaks in the applied load. Each fracture event constitutes a break in brittle material which releases acoustic energy into the structure in the form of a broadband pulse having a frequency spectrum covering a band of from 20 kHz to several MHz. The acoustic energy released at each fracture event propagates through the structural member 10, and may be represented by wavefronts 16 spreading out through the member in a manner analogous to ripples in a pond.

In this embodiment, the structural member 10 carries three acoustic transducers 18 bonded to the surface of the member 10 to receive acoustic signals which have travelled through the member 10 from the source of the energy. It will be noted that the transducers 18 are at spaced apart locations. In the general case, therefore, each is at a different distance from the crack tip so that acoustic energy due to a fracture event will reach each sensor at a different time. Measurement of the times of arrival of an acoustic transient offers a means of identifying a fracture and of defining the location of the crack tip using trigonometric calculations based on the relative times of arrival.

It will be appreciated that in a practical situation such as on an aircraft, transducer output pulses or wave packets corresponding to acoustic energy from a fracture event will be accompanied by general background noise from both mechanical and electrical sources such as pumps, actuators and so on.

The transducers in this example are piezoelectric sensors having a resonant frequency in the range of from 20 kHz to 2 MHz. For aluminium structures, it has been found that a resonant frequency in the region of 300 kHz is suitable. For steel and fibre reinforced composites, a lower frequency, e.g. in the range of 50 to 150 kHz is preferred. It follows that the electrical signals fed via cables 20 from the transducers 18 due to fracture events take the form of wave packets with a fundamental frequency equal to the resonant frequency of the sensors.

Preferred apparatus in accordance with the invention is illustrated in block diagram form in FIG. 2. Referring to FIG. 2, the apparatus has a large number N of channels (1) to (N) each having a transducer 18, a preamplifier unit 22 coupled to and located physically within a few meters of the transducer 18 and, coupled to the output of the preamplifier 22, a signal conditioning stage 24 in the form of a rectifying logarithmic amplifier. In each channel the logarithmic amplifier feeds one channel of a pulse processor unit having an A-to-D converter (ADC) 26 and a field programmable gate array (FPGA) 28. These, together with a first-in first-out (FIFO) memory 30 common to all N channels, constitute the first part of a pulse processor unit for processing digital representations of the pulses obtained from the transducers 18 to form data bursts in order to isolate said data bursts representing the pulses corresponding to fracture events in the structural member. In this example, the signal conditional stages 24, the ADCs 26, the FPGAs 28 and the FIFO memory 30 are all contained in a real time signal processing module 32 having a timing input 34 providing common timing to all N channels, and a data output 36 for connection to the remaining part of the pulse processor unit in the form of a data processor 38.

To follow the passage of signals from the transducers 18 to the output 36 from the FIFO memory 30, the signals from each transducer 18 are fed to a respective preamplifier 22. A pulse corresponding to a fracture event typically takes the form of a wave packet like that shown in FIG. 3. Each preamplifier 22 has filtering to define a passband containing the resonant frequency of the transducer 18 which, in this example, is 300 kHz. The signal conditioning stage 24 further amplifies the wave packets and, in addition to providing a logarithmic representation of the incoming signal amplitude, rectifies the signal and produces a smoothed output following the peaks of the rectified waveform, as shown in FIG. 4. It should be noted that FIG. 4 is a composite waveform diagram in the sense that it shows, firstly, the rectified 300 kHz waveform, as well as the smoothed output signal which, as shown by the enlargement in FIG. 4, is an envelope waveform following the 300 kHz peaks.

Next, the envelope waveform from the signal conditioning stage 24 is passed to the ADC 26 which samples the burst envelope in the manner shown in FIG. 5 to produce a digital representation for processing in the FPGA 28. The output of the FPGA 28 performs burst feature extraction for each received burst exceeding an amplitude threshold $A_{th}$. The features extracted are:

$T_{START}$ (the start time defined as the instant when the burst crosses the threshold $A_{th}$)

$T_{PEAK}$ (the instant at which the peak burst amplitude occurs)

$T_{END}$ (the end time of the bursts. Defined only after the burst amplitude has remained below $A_{th}$ for a user defined period $T_{WAIT}$ (typically 500 µs))

Peak Amplitude

Envelope Area $T_R$ (rise time=$T_{PEAK}-T_{START}$)

$T_D$ (burst duration=$T_{END}-T_{START}$)

Note that $T_{END}$ is only recorded if, during a further user-defined period $T_{WAIT}$, typically 500 µs, the burst amplitude remains below $A_{th}$.

The extracted features form a burst descriptor for each burst, which is fed to the FIFO memory 30 which acts as a buffer for further processing by the data processing unit 38.

Figure 6:
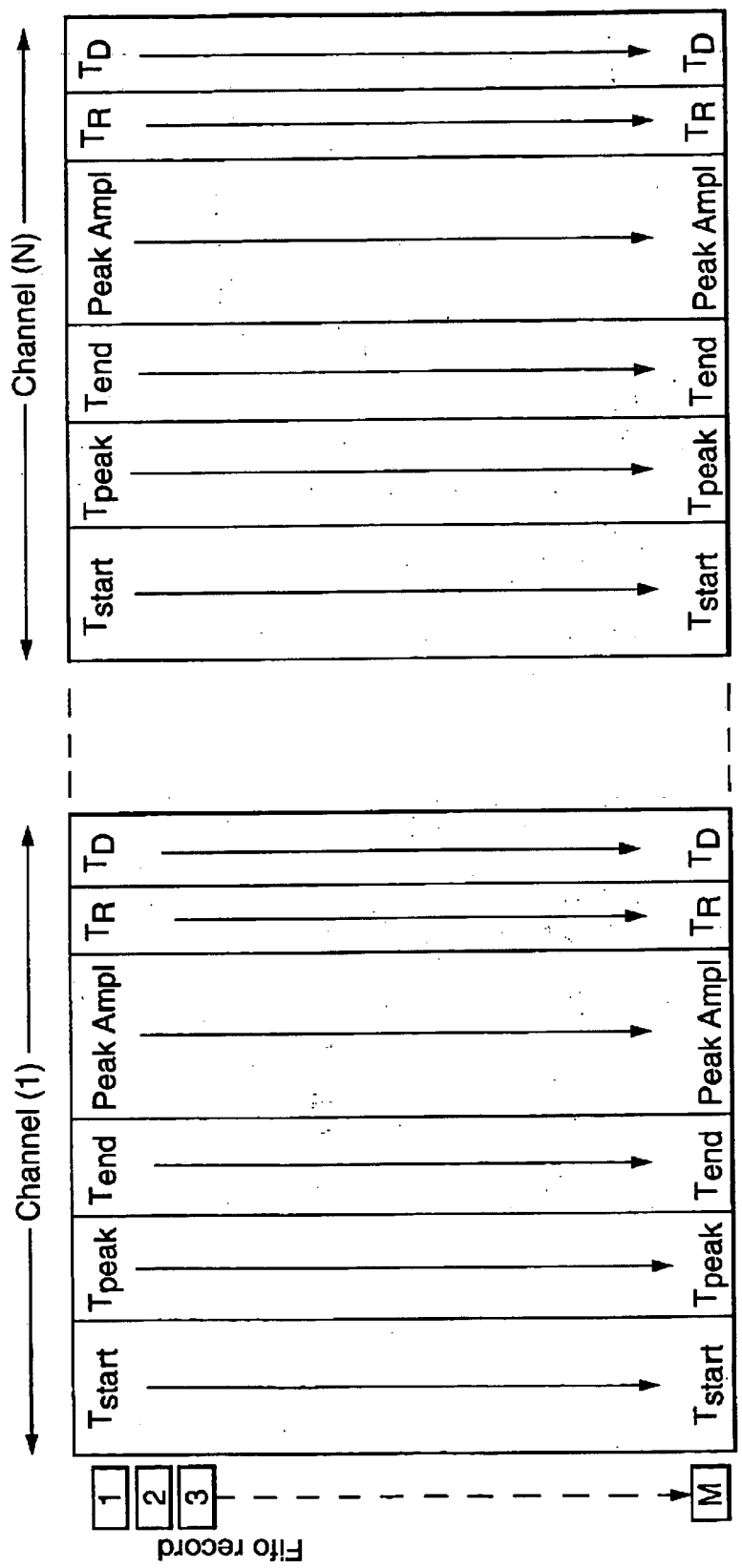
FIG. 6 is a schematic representation of pulse descriptors stored as data stacks in a FIFO buffer forming part of the apparatus of FIG. 2.

The organisation of the FIFO stacks is shown in FIG. 6. The extracted features $T_{START}$, etc. for each of the N channels are stored for each burst in each channel, as shown. At any one time, M bursts from each channel are stored.

Processing of the buffered pulse descriptors by the data processing unit 38 proceeds in two main stages. Firstly, groups of bursts such as those in channels (1) to (4) are subjected to a preliminary burst validation process to define a group of data bursts having characteristics likely to represent the same fracture events in the structural member corresponding to the respective group of transducers. This group of data bursts are then further analysed over a long period of time to identify repetitions of a particular delta-t pattern, each such pattern comprising time difference values between pulses within the group in a second stage to ensure the data burst in the group of data bursts did originate from the same fracture event to create a validated data burst.

Figure 7:
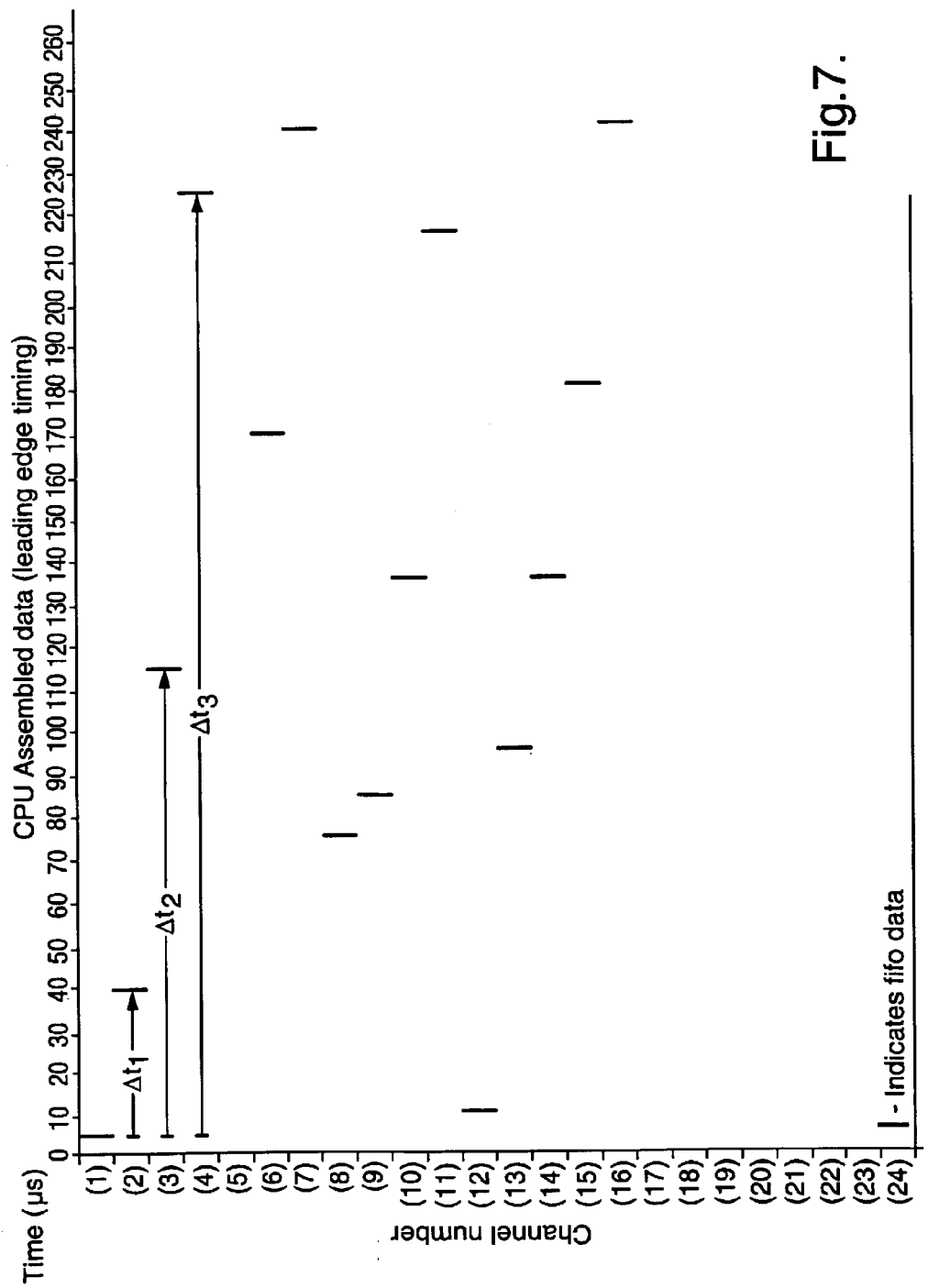
FIG. 7 is a diagram illustrating typical timing patterns of data bursts occurring in different channels of the apparatus of FIG. 2.

The data stored in the FIFO 30 provides a record of bursts received by the transducers 18 over a short period of time, as shown in FIG. 7. This data is being constantly refreshed as new bursts are received, and the size of the FIFO memory 30 is sufficient to allow preliminary burst validation processing by the data processing unit 38 of the stored data before it is overwritten by the new data. FIG. 7 shows a typical sequence of bursts from 24 transducers 18. Each bar in the graph indicates data stored in the FIFO memory 30 as extracted features of a respective pulse. In this example, channels (1) to (4) correspond to first group of four transducers 18, channels (5) to (11) to a further seven transducers, channels (12) to (16) to a further group of four transducers. The other channels in this example are not used. Each group of transducers 18 is mounted on a respective structural member. Taking channels (1) to (4), it will be seen that during the time interval represented by the graph at this particular instant, (the interval is typically 400 µs long), the first event which might correspond to a fracture occurs in channel (1). For the first group, therefore, of transducers 18, assuming the maximum time difference between the first and last events in the group is set at 400 µs, there are further bursts occurring at, respectively, 35, 110, and 220 µs after the first burst. In the general case, these time differences are designated $\Delta t_1$, $\Delta t_2$ and $\Delta t_3$, as shown in FIG. 7. Thus a group of data bursts likely to represent the same fracture event is formed.

Subsequent processing occurs in the data processing unit 38. Processing unit 38 comprises a CPU 40, associated RAM 41, a disk storage unit 42 for non-volatile storage of data and a communications interface 43 which delivers messages to a communications output 44 allowing notification of significant detected events and for confirming system operation. Such communications may take place as e-mails transmitted over a radio link such as a cellular telephone link in the case of remote structure monitoring. This link is preferably bi-directional to allow system configuration.

The CPU 40 is programmed to evaluate the burst descriptors corresponding to bursts in each group of channels (1) to (4), (5) to (8), etc. in a moving time window which may be typically 32 or 64 ms long. When a minimum number of bursts (e.g. 2, 3, or 4 depending on the geometry of the structure being monitored) from different respective transducers occurs within the window, the corresponding group of burst descriptors is defined in delta-t terms. To explain with reference to FIG. 7, the delta-t values are measured, as mentioned above, for channels (1) to (4) as $\Delta t_1=35$ µs, $\Delta t_2=110$ µs and $\Delta t_3=220$ µs. A further condition is then imposed, which is that the largest delta-t value should not be greater than a predetermined time interval, in this case 400 µs.

Further analysis of the group of data bursts is then undertaken.

Figure 8:
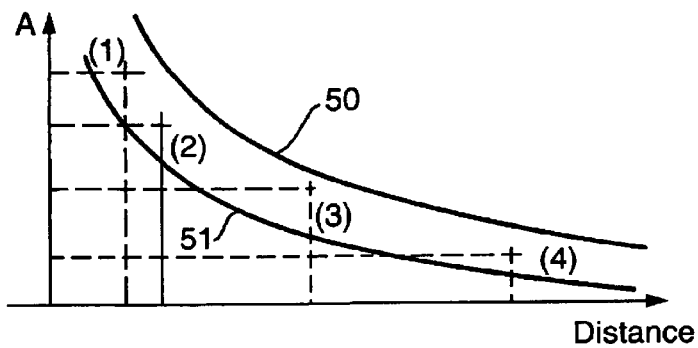
FIG. 8 is an amplitude profile graph.

A further applied condition is an amplitude condition. Depending on the nature of the structure and placement of transducers, successive bursts from the different transducers of a group due to a fracture event can be expected to conform to a predetermined range of amplitude profiles due to decay of the acoustic energy with increasing distance from the source. Thus, it is possible to apply an amplitude condition for the bursts such as a decaying amplitude profile (decaying with increasing distance) as shown in FIG. 8.

In this example bursts occurring in channels (1), (2), (3) and (4) are shown, plotted on the basis of amplitude against time. By setting upper and lower amplitude threshold curves 50, 51, as shown, bursts can be accepted as satisfying the amplitude condition providing the burst amplitudes fall between the curves. It will be understood that alternative amplitude profiles may be specified. Non-acoustic data may be used to restrict validation of bursts or system generation to episodes during which damage is likely to occur.

Having performed the above selection processes, the group of bursts in channels (1) to (4) is defined as a validated data burst. The processing described above occurs in real time. Each validated data burst is stored as a burst descriptor in RAM 41, the burst descriptor having the following elements:

Date

Time

Transducer Group

Hit Order (order in which the transducers receive the pulses)

Amplitudes (one per channel)

Delta-t Values (one per channel)

Burst Rise Times

Burst Duration (one per channel)

NAD (non acoustic data)

Burst Area (energy)

These burst descriptors are stored for a limited time in RAM 41, and are only saved further if the relevant bursts pass through a further processing stage to be described below. The non acoustic data typically consists of environmental parameters such as concurrent structure load, strain, and temperature measurements.

Figure 9:
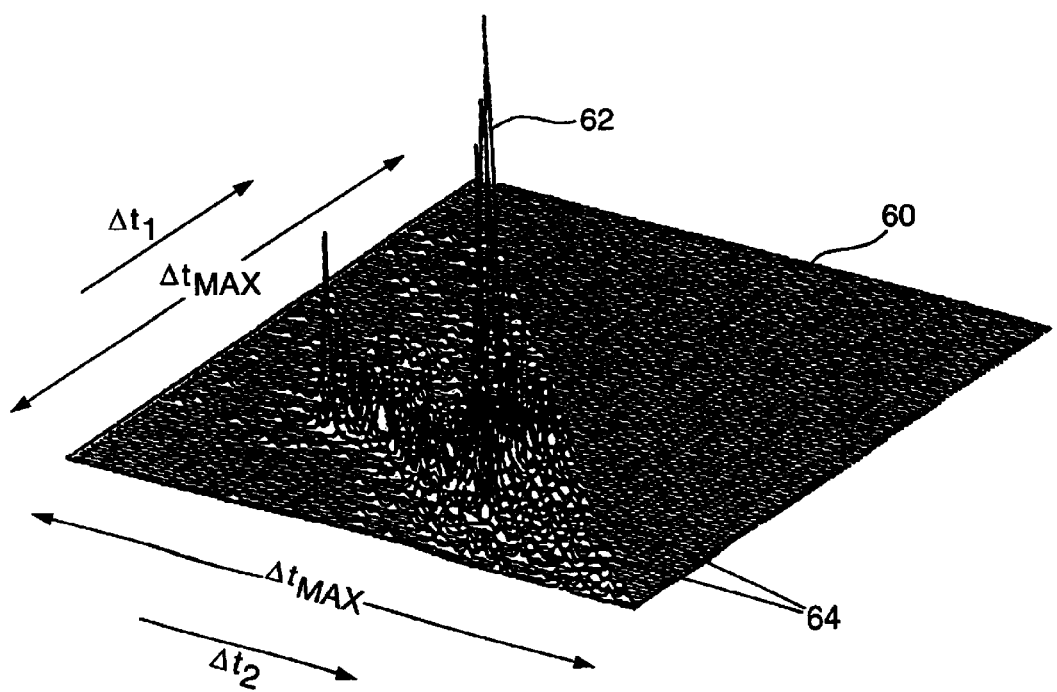
FIG. 9 is a perspective representation of a time-difference (delta-t) matrix formed in RAM in the apparatus of FIG. 2.

The next stage of processing in the data processing unit 38 is a filtering process which comprises incrementing a delta-t matrix formed in RAM 41. Referring to FIG. 9 which shows a two-dimensional matrix 60 as the basis of a time difference filter, the matrix spans a maximum delta-t ($\Delta t_{MAX}$) value in each dimension, corresponding to the maximum allowed interval between the first and last pulses of a validated burst. The matrix 60 is divided into cells, the cell density determining the time difference resolution. Thus, the matrix has a predetermined grain size in each dimension. Each of the cells corresponds to a particular value of $\Delta t_1$ and $\Delta t_2$. Each validated burst increments the cell corresponding to the values of $\Delta t_1$ and $\Delta t_2$ for that burst. If, therefore, over a period of time, validated bursts each having the same $\Delta t_1$ and $\Delta t_2$ values are received, the corresponding cell acquires a value higher than other cells. By setting a cell value threshold covering at least a portion of the matrix, it is possible, therefore, to detect repetition of bursts with corresponding delays between bursts. It is these bursts which are most likely to represent a fracture event, since progressive micro fractures, as described above, give rise to successive acoustic transients emanating from the same point or a slowly moving point on the respective structural member. Cell values are indicated in the diagrammatic representation of FIG. 9 as projections above a base plane. Projection 62 represents a high intensity crack, and neighbouring peaks of lower amplitude may represent associated subsidiary cracks or the arrival of different wave modes or timing variations resulting from variations in burst signal amplitude. Smaller projections, such as those indicated at 64 are treated as indicating background noise. Preferably, an unwanted general increase in cell values across the whole matrix due to noise are eliminated by decrementing all of the cells periodically so that only the more rapidly incremented cells reach the predetermined cell value threshold.

The cell value threshold may be viewed as a plane arranged above and parallel to the base plane 60 shown in FIG. 9.

When a cell of the matrix 60 reaches the cell value threshold, the burst descriptor of at least one of the bursts causing the cell value threshold to be reached (preferably only the most recent such burst) is stored to non-volatile storage. This represents a significant event indication signal; referred to as a burst signal record. The cell value is then set back to zero.

Figure 10:
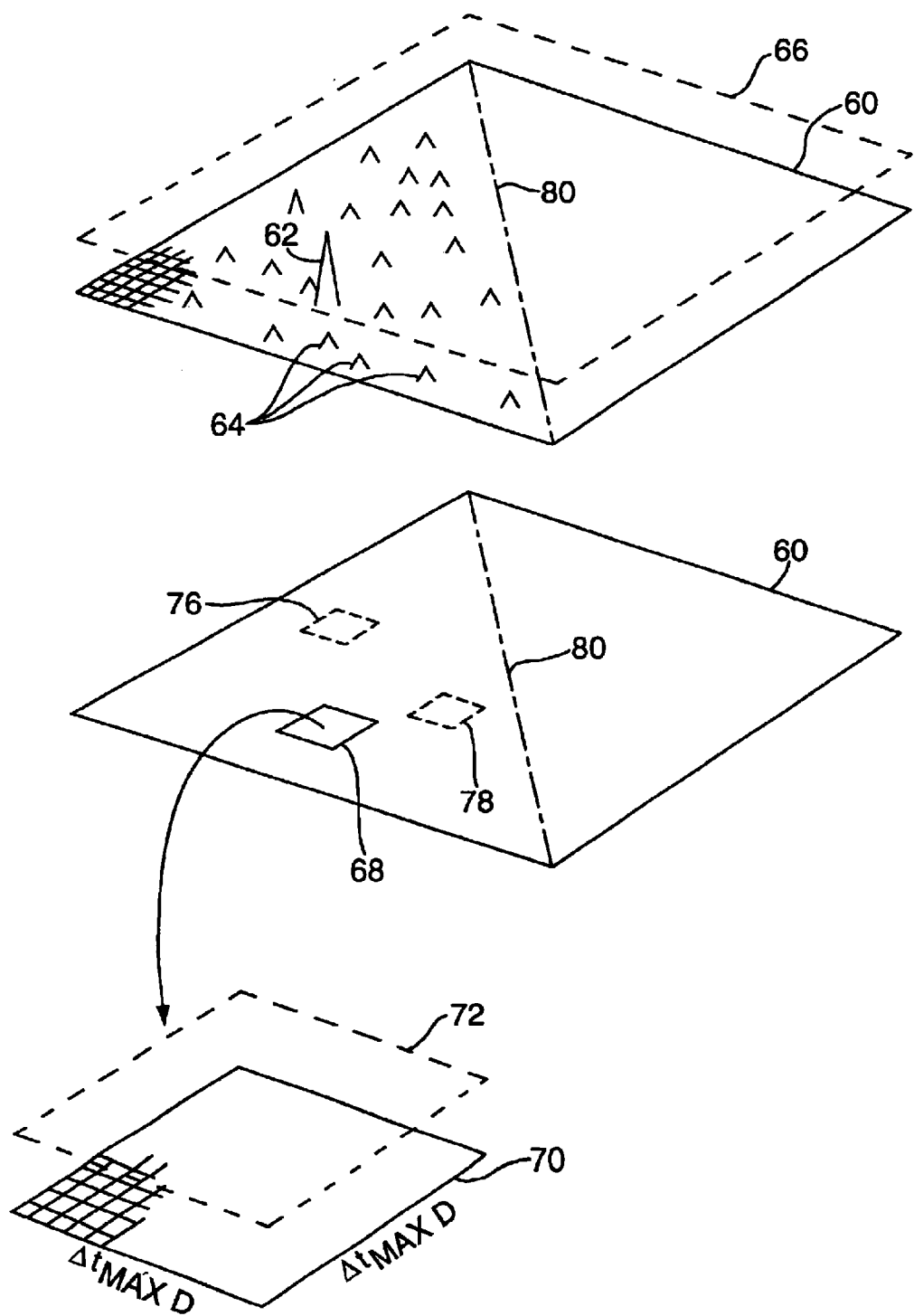
FIG. 10 is diagrammatic representation of the derivation of a daughter filter from the primary filter formed by the matrix shown in FIG. 9.

The sensitivity of the filter represented by the matrix 60 is dependent on its threshold 66 and the grain size. The threshold needs to be maintained at a relatively low value to allow identification of further significant events after they enter the matrix. Referring to FIG. 10, to avoid masking of new such significant events by excess data from the previously identified significant event (represented by cell value 62), the system is configured to create a so-called daughter matrix 70. This may be performed dynamically and automatically or in response to user intervention. Like the matrix 60 (hereinafter referred to as the primary matrix), is a time-difference matrix with a range of time difference (delta-t) values corresponding to a small portion of the primary matrix 60. This portion is the portion containing the cell the value of which reached the threshold 66. Daughter matrix 70 typically has a higher threshold value 72 and its own grain size (resolution) calculated to produce a 10 to 100-fold decrease in the data rate due to the identified fracture. This is acceptable because, effectively, the significant event has been recognised and can be removed from the stored set of data, thereby reducing the volume of stored data. Detection of further significant events can consequently be enhanced whilst monitoring of the first-identified event continues using the daughter filter or daughter matrix 70.

Similar daughter matrices or filters can be formed from the primary matrix in different delta-t locations, as indicated, for instance, by portions 76, 78 in FIG. 10.

As it does in the case of the primary matrix 60, the CPU may form a periodic decrement across the whole of the daughter matrix 70 (decrementing each cell by value 1) to suppress noise.

Once a daughter matrix 70 is formed, burst descriptors with corresponding delta-t values are directed to the daughter matrix 70 in place of the primary matrix 60, where they are subjected to a different filtering characteristic due to the higher threshold 72. Automatic creation of the daughter matrix may be achieved, for instance, by monitoring the rate of cell value increase or by forming a table of burst hit orders for each cell with time. Thus, in conjunction with or separately from delta-t monitoring, validated bursts having a common "hit" (pulse) sequence in terms of the order in which transducers produce pulses to form the bursts, may be used to generate a count of hits within a period. A hit rate may also be calculated by dividing the number of hits by the period in which they are obtained. Automatic daughter matrix creation may also be triggered when the rate of threshold crossings in a cell exceeds a predetermined unit, bearing in mind that all cell values are decremented periodically to reduce noise. Depending on the pattern of validated bursts obtained when the apparatus is used to monitor a particular structure, the burst descriptors may be used in these different ways, i.e. not necessarily using a cell value threshold, to achieve efficient isolation of significant fracture events. These may be viewed as variations seeking to achieve the best performance for a given processing and storage capability.

A refinement in the derivation of delta-t values is the use of not only the leading edges (represented by $T_{START}$) of the pulses processed by the A to D converter 26 (see FIGS. 2 and 5), but also the peak times ($T_{PEAK}$) for the highest amplitude pulses in preferred time intervals. In the preferred system leading edge and peak timing run simultaneously. Leading edge timing is preferred due to its greater accuracy, but in the presence of increased background noise, peak timing provides an alternative source correlation. The primary matrix 60 (as shown in FIGS. 9 and 10) may be divided into two triangles by a diagonal line 80 between opposite corners, the cells in one triangular area being incremented by data based on leading edge delta-t values, and the other triangular area being incremented on the basis of delta-t values calculated from peak timings.

The preferred apparatus in accordance with the invention has sufficient processing power and memory resource to create several primary matrices for both leading edge and peak delta-t timing, and to create several secondary or daughter matrices or filters from each such primary matrix or filter. This allows several different structural members or structures to be monitored in parallel.

As mentioned above with reference to FIG. 2, the apparatus provides for communication of defect data to a remote location. Typically, a message is produced when a daughter matrix is formed or first used, such messages being transmitted via a modem or the Internet. Additionally, the preferred apparatus provides a connection for integration of the apparatus in a local area network (LAN) for high speed real-time data transfer. In this way, it is possible for information produced by the apparatus to be accessed at different locations.

What is claimed is:

1. A method of detecting and monitoring damage in a structure comprising:
   receiving continuously over a period of time electrical signals from a plurality of acoustic transducers, carried by the structure, configured to receive acoustic emissions from the structure when the structure is submitted to stress; and in a pulse processor,
(a) forming digital representations pulses from the electrical signals to form data bursts,
(b) selecting data bursts that occur in a predetermined time window to form a group of data bursts,
(c) deriving, for each of the selected data bursts, delta-t values representing the differences between the times of occurrence of the pulses represented by the selected data bursts in the group, the delta-t values forming a delta-t pattern, and
(d) generating a significant event indication signal when the delta-t pattern is repeated to a predetermined degree in different groups of selected data bursts.

2. A method according to claim 1, wherein the step of generating a damage indication signal includes filtering the delta-t values in a primary filtering step having a first filter parameter value, the method further comprising deriving a second filter parameter value tailored to the characteristics of at least one of the groups of data bursts giving rise to the significant event indication signal and subjecting subsequent corresponding groups of data bursts to a secondary filtering step in place of the primary filtering step whilst continuing to subject other incoming bursts to the primary filtering step to continue to form groups of data bursts for the detection of further repeated delta-t patterns, the secondary filtering step having the said second filter parameter value.

3. A method according to claim 2, wherein the first and second filter parameter values are count thresholds, the first filter parameter value being a lower count threshold that the secondary filter parameter value.

4. A method according to claim 2, wherein the groups of data bursts subjected to the secondary filtering step are those having a delta-t pattern substantially corresponding to that of groups giving rise to the significant event indication signal.

5. A method according to claim 2, further comprising deriving an additional second filter parameter value respectively tailored to the characteristics of the groups of data bursts giving rise to each successive significant event indication signal, and subjecting subsequent corresponding bursts to secondary filtering steps having respective second filter parameter values whilst continuing to subject bursts which do not substantially correspond to one of the significant event indication signals to the primary filtering step.

6. A method according to claim 1, including incrementing cells in an n-dimensional time difference matrix over the said predetermined time window in response to groups of data bursts according to n delta-t values associated with each group, and generating a significant event indication signal when the value of one or more of the cells exceeds a predetermined threshold, n being at least 2.

7. A method according to claim 6, wherein n equals 2.

8. A method according to claim 2, wherein the primary filtering step uses at least a portion of the time difference matrix, and each secondary filtering step uses a smaller portion of the matrix, the smaller portion corresponding to the delta-t pattern of the at least one group giving rise to a significant event indication signal.

9. A method according to claim 1, including selecting for further processing only groups of data bursts meeting a predetermined condition or conditions, the condition or conditions for selecting a group being at least one of:
(a) the group excites a minimum number of sensors in the sensing array,
(b) the timings between successive sensors being excited all fall within a predetermined time period, and
(c) signal amplitudes on successively excited sensors in a sensing array fall within predetermined bounds.

10. A method according to claim 1, wherein the signals received from the transducers are narrowband signals at a frequency in the range of from 100 kHz to 1 MHz.

11. Apparatus for use in the detection and monitoring of damage in a structure, comprising:
a plurality of acoustic transducers mounted on said structure and configured to receive acoustic emissions from the structure when the structure is submitted to stress;
a signal conditioning stage coupled to the transducers and arranged to derive pulses corresponding to acoustic events sensed by the transducers; and
a pulse processor unit comprising an analogue-to-digital converter (ADC) stage coupled to the signal conditioning stage and a digital signal processing stage including selection means configured to select, from digitised signals received from the ADC stage, digitised pulses to form data bursts means for selecting a group of data bursts occurring in a predetermined time window, means arranged to derive, for each selected data bursts in the group, delta-t values representing the differences between the times of occurrence of the bursts, the delta-t values forming a delta-t pattern, and
a correlator arranged to generate a significant event indication signal when the delta-t pattern is repeated to a predetermined degree in different groups data bursts.

12. Apparatus according to claim 11, wherein the correlator comprises a primary filter having a first burst filtering characteristic and a storage device coupled to receive burst information resulting from data bursts filtered in the primary filter means, and means arranged to form at least one secondary filter in response to burst information corresponding to a detected significant event, the secondary filter having a second burst filtering characteristic tailored to select groups of data bursts emanating from the detected significant event, the processor unit being configured such that groups emanating from the detected event are thereafter directed for filtering by the secondary filter prior to the resulting burst information being fed to the storage device.

13. Apparatus according to claim 12, wherein the first and second filtering characteristics include count thresholds, that of the second characteristic having a higher count threshold than that of the first characteristic.

14. Apparatus according to claim 11, wherein the correlator comprises means forming an n-dimensional group of data bursts arrival time matrix, means arranged to increment cells of the matrix according to n timing values associated with each group of data bursts, and means arranged to generate the significant event indication signal when the value of one or more of the cells exceeds a predetermined threshold, n being at least 2.

15. Apparatus according to claim 12, wherein the primary filter means comprise the burst arrival time matrix and the secondary filter comprises a portion of the said matrix, which portion is taken from primary filter after generation of the significant event indication signal.

16. Apparatus according to claim 14, wherein n equals 2.

17. Apparatus according to claim 11, wherein the transducers are resonant transducers having a resonant frequency in the range of 20 kHz and 2 MHz.

18. Apparatus according to claim 11, wherein the signal conditioning stage converts signals received from the transducers as wave packets corresponding to acoustic events in the structure to pulses representing rectified envelopes of the wave packets.

19. Apparatus according to claim 11, wherein the pulse processor unit comprises a gate array arranged to generate in real time burst descriptors defining wave packets from the transducers; a buffer for buffering the burst descriptors; a CPU, RAM and non-volatile storage device combination programmed (a) to perform preliminary pulse selection and data burst formation based on the buffered pulse descriptors, (b) to act as said correlator correlating data bursts, and (c) to store burst information representing detected significant event over a monitoring period.

20. A structure which is monitored for damage due to cyclic loading, wherein the structure comprises a plurality of structural members, a plurality of groups of acoustic transducers configured to receive acoustic emissions from the structure when the structure is submitted to stress, each group mounted on a respective structural member, and a signal processing unit coupled to the transducers and arranged to detect groups of data bursts each comprising data bursts representing pulses in signals received from respective transducers of one of the groups of transducers during a sampling time interval, and to derive, for each of the data bursts, timing information relating to the times of arrival of the data burst forming the group, the signal processing unit further comprising a correlator arranged to generate a significant event indication signal when the timing pattern is repeated to a predetermined degree in different groups of data bursts from the said group of transducers.

21. A structure according to claim 20, wherein the signal processing unit is configured to process signals from the transducers continuously over at least several hours, to generate a significant event indication signal by real time filtering of the data bursts in a primary filter based on predetermined data burst signal features and pulse arrival times, to define automatically at least one secondary filter adaptively based on the burst signal features of at least one of the groups giving rise to the significant event indication signal, to divert subsequent groups corresponding to the significant event indication signal from the primary filter to the secondary filter, whereby subsequent groups unrelated to the significant event indication signal continue to be filtered in the primary filter for generating further significant event indication signals emanating from different damage features in the structure.

* * * * *